(12) United States Patent
Krafft et al.

(10) Patent No.: US 7,893,193 B2
(45) Date of Patent: Feb. 22, 2011

(54) METHOD FOR MAKING A CHLOROHYDRIN

(75) Inventors: Philippe Krafft, Rhode Saint Genese (BE); Patrick Gilbeau, Braine-le-Comte (BE); Dominique Balthasart, Brussels (BE); Valentine Smets, Brussels (BE)

(73) Assignee: Solvay (Société Anonyme), Brussels (BE)

( * ) Notice: Subject to any disclaimer, the term of this patent is extended or adjusted under 35 U.S.C. 154(b) by 309 days.

(21) Appl. No.: 11/914,836

(22) PCT Filed: May 19, 2006

(86) PCT No.: PCT/EP2006/062439

§ 371 (c)(1),
(2), (4) Date: Nov. 19, 2007

(87) PCT Pub. No.: WO2006/100313

PCT Pub. Date: Sep. 28, 2006

(65) Prior Publication Data

US 2009/0131631 A1    May 21, 2009

Related U.S. Application Data

(60) Provisional application No. 60/734,635, filed on Nov. 8, 2005, provisional application No. 60/734,657, filed on Nov. 8, 2005, provisional application No. 60/734,636, filed on Nov. 8, 2005, provisional application No. 60/734,627, filed on Nov. 8, 2005, provisional application No. 60/734,634, filed on Nov. 8, 2005, provisional application No. 60/734,658, filed on Nov. 8, 2005, provisional application No. 60/734,637, filed on Nov. 8, 2005, provisional application No. 60/734,659, filed on Nov. 8, 2005.

(30) Foreign Application Priority Data

May 20, 2005    (EP)    .................................. 05104321
May 20, 2005    (FR)    .................................... 0505120

(51) Int. Cl.
    *C08G 61/00*    (2006.01)
(52) U.S. Cl. ...................... 528/397; 549/514; 549/518; 549/512; 568/841; 568/844
(58) Field of Classification Search ................. 528/397; 549/512, 518; 568/841, 844
    See application file for complete search history.

(56) References Cited

U.S. PATENT DOCUMENTS 2,060,715 A    11/1936    Arvin
(Continued)

FOREIGN PATENT DOCUMENTS

CA    1119320    8/2003
(Continued)

OTHER PUBLICATIONS

Gibson., "The Preparation, Properties, and Uses of Glycerol Derivatives. Part III. The Chlorohydrins", Chemistry and Industry, Chemical Society, pp. 949-975, 1931.
(Continued)

*Primary Examiner*—Randy Gulakowski
*Assistant Examiner*—Shane Fang
(74) *Attorney, Agent, or Firm*—Oblon, Spivak, McClelland, Maier & Neustadt, L.L.P.

(57) ABSTRACT

Process for preparing a chlorohydrin, comprising the following steps:
(a) a polyhydroxylated aliphatic hydrocarbon, an ester of a polyhydroxylated aliphatic hydrocarbon or a mixture thereof is reacted with a chlorinating agent and an organic acid so as to give a mixture containing the chlorohydrin and esters of the chlorohydrin
(b) at least part of the mixture obtained in step (a) is subjected to one or more treatments in steps subsequent to step (a)
(c) polyhydroxylated aliphatic hydrocarbon is added to at least one of the steps subsequent to step (a), so as to react, at a temperature greater than or equal to 20° C., with the esters of the chlorohydrin, so as to form, at least partly, esters of the polyhydroxylated aliphatic hydrocarbon.

14 Claims, 1 Drawing Sheet

U.S. PATENT DOCUMENTS

Figure 1:
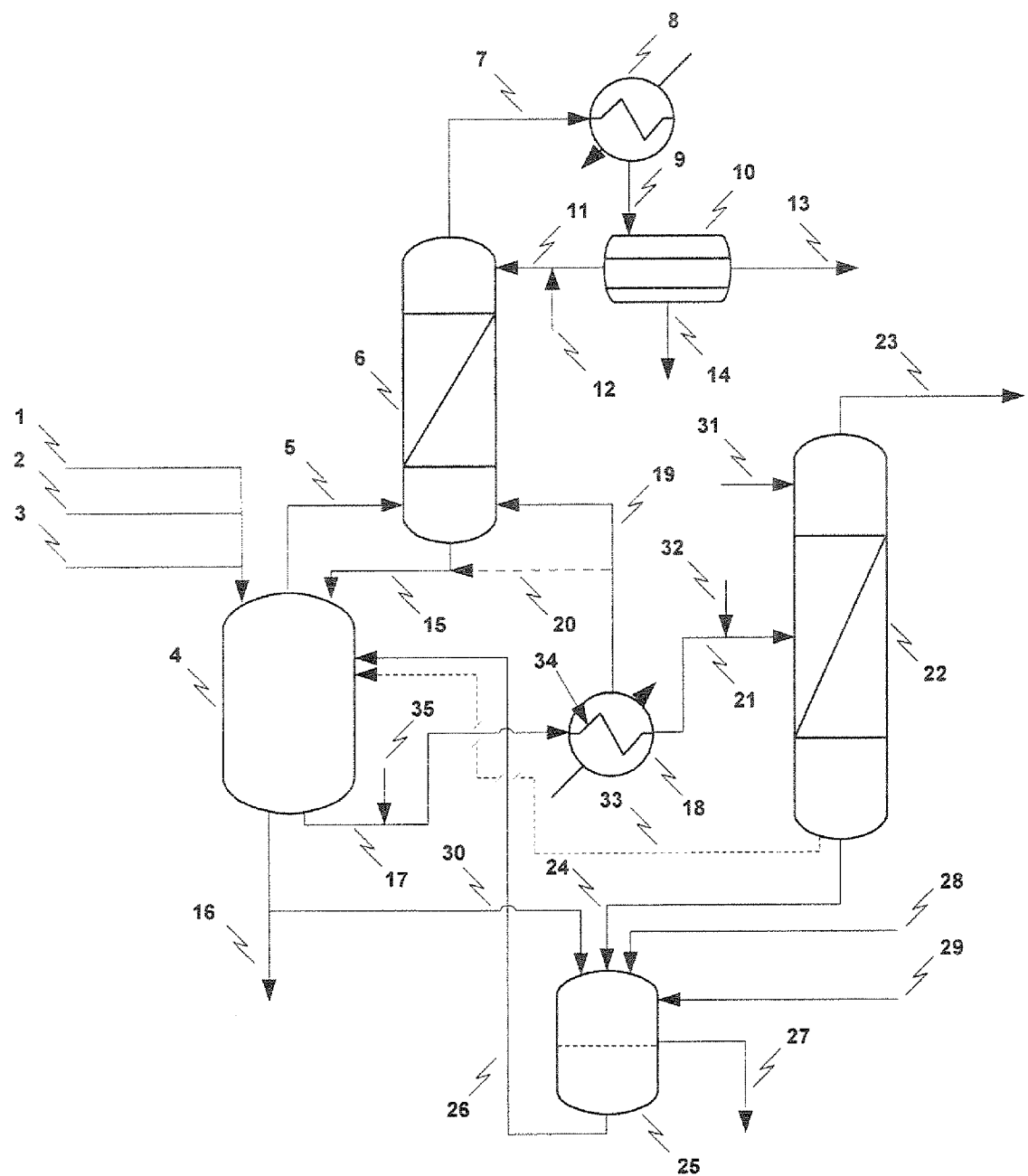

| | | | |
|---|---|---|---|
| 2,063,891 | A | 12/1936 | Dreyfus |
| 2,144,612 | A | 1/1939 | Britton et al. |
| 2,198,600 | A | 4/1940 | Britton et al. |
| 2,248,635 | A | 7/1941 | Marple et al. |
| 2,319,876 | A | 5/1943 | Moss |
| 2,444,333 | A | 6/1948 | Castan |
| 2,726,072 | A | 12/1955 | Hermann |
| 2,811,227 | A | 10/1957 | O'Connor |
| 2,829,124 | A | 4/1958 | Napravnik et al. |
| 2,860,146 | A | 11/1958 | Furman et al. |
| 2,876,217 | A | 3/1959 | Paschall |
| 2,945,004 | A | 7/1960 | Greenlee |
| 2,960,447 | A | 11/1960 | Anderson et al. |
| 3,026,270 | A | 3/1962 | Robinson, Jr. |
| 3,061,615 | A | 10/1962 | Viriot et al. |
| 3,135,705 | A | 6/1964 | Vandenberg |
| 3,158,580 | A | 11/1964 | Vandenberg |
| 3,158,581 | A | 11/1964 | Vandenberg |
| 3,247,227 | A | 4/1966 | White |
| 3,341,491 | A | 9/1967 | Robinson, et al. |
| 3,355,511 | A | 11/1967 | Schwarzer |
| 3,385,908 | A | 5/1968 | Schwarzer |
| 3,457,282 | A | 7/1969 | Polak et al. |
| 3,711,388 | A | 1/1973 | Gritzner |
| 3,839,169 | A | 10/1974 | Moyer |
| 3,865,886 | A | 2/1975 | Schindler et al. |
| 3,867,166 | A | 2/1975 | Sullivan |
| 3,954,581 | A | 5/1976 | Carlin |
| 3,968,178 | A | 7/1976 | Obrecht et al. |
| 4,220,529 | A | 9/1980 | Daude-Lagrave |
| 4,390,680 | A | 6/1983 | Nelson |
| 4,405,465 | A | 9/1983 | Moore et al. |
| 4,415,460 | A | 11/1983 | Suciu et al. |
| 4,499,255 | A | 2/1985 | Wang et al. |
| 4,595,469 | A | 6/1986 | Foller |
| 4,609,751 | A | 9/1986 | Hajjar |
| 4,634,784 | A | 1/1987 | Nagato et al. |
| 4,960,953 | A | 10/1990 | Jakobson et al. |
| 4,973,763 | A | 11/1990 | Jakobson et al. |
| 5,041,688 | A | 8/1991 | Jakobson et al. |
| 5,286,354 | A | 2/1994 | Bard et al. |
| 5,344,945 | A | 9/1994 | Grunchard |
| 5,359,094 | A | 10/1994 | Teles et al. |
| 5,445,741 | A | 8/1995 | Dilla et al. |
| 5,567,359 | A | 10/1996 | Cassidy et al. |
| 5,578,740 | A | 11/1996 | Au et al. |
| 5,710,350 | A | 1/1998 | Jeromin et al. |
| 5,731,476 | A | 3/1998 | Shawl et al. |
| 5,744,655 | A | 4/1998 | Thomas et al. |
| 5,779,915 | A | 7/1998 | Becker et al. |
| 5,908,946 | A | 6/1999 | Stern et al. |
| 5,993,974 | A | 11/1999 | Fukushima et al. |
| 6,142,458 | A | 11/2000 | Howk |
| 6,270,682 | B1 | 8/2001 | Santen et al. |
| 6,288,248 | B1 | 9/2001 | Strebelle et al. |
| 6,288,287 | B2 | 9/2001 | Ueoka et al. |
| 6,350,922 | B1 | 2/2002 | Vosejpka et al. |
| 6,740,633 | B2 | 5/2004 | Norenberg et al. |
| 7,126,032 | B1 | 10/2006 | Aiken |
| 7,128,890 | B2 | 10/2006 | Ollivier |
| 865,727 | A1 | 9/2007 | Queneau |
| 2001/0014763 | A1 | 8/2001 | Ueoka et al. |
| 2003/0209490 | A1 | 11/2003 | Camp et al. |
| 2004/0179987 | A1 | 9/2004 | Oku et al. |
| 2004/0232007 | A1 | 11/2004 | Carson et al. |
| 2005/0261509 | A1 | 11/2005 | Delfort et al. |
| 2006/0052272 | A1 | 3/2006 | Meli et al. |
| 2006/0079433 | A1 | 4/2006 | Hecht et al. |
| 2007/0112224 | A1 | 5/2007 | Krafft et al. |
| 2008/0045728 | A1* | 2/2008 | Kruper, Jr. et al. .......... 549/518 |
| 2008/0154050 | A1 | 6/2008 | Gilbeau |
| 2008/0281132 | A1 | 11/2008 | Krafft et al. |
| 2009/0022653 | A1 | 1/2009 | Strebelle et al. |
| 2009/0198041 | A1 | 8/2009 | Krafft et al. |

FOREIGN PATENT DOCUMENTS

| | | |
|---|---|---|
| CN | 1296003 A | 5/2001 |
| DE | 58396 | 8/1891 |
| DE | 197 308 | 11/1906 |
| DE | 238 341 | 3/1908 |
| DE | 1 041 488 | 10/1958 |
| DE | 1 075 103 | 2/1960 |
| DE | 1 226 554 | 10/1966 |
| DE | 30 03 819 | 8/1981 |
| DE | 216 471 | 6/1983 |
| DE | 32 43 617 | 5/1984 |
| DE | 37 21 003 | 6/1987 |
| DE | 102 03 914 | 1/2002 |
| DE | 102 54 709 | 6/2004 |
| DE | 238341 | 3/2008 |
| DE | 197 309 | 4/2008 |
| EM | 436093 | 8/2000 |
| EP | 180 668 | 1/1906 |
| EP | 0 296 341 | 12/1988 |
| EP | 0 347 618 | 12/1989 |
| EP | 0 421 379 | 4/1991 |
| EP | 0 518 765 | 12/1992 |
| EP | 0 522 382 | 1/1993 |
| EP | 0 535 949 | 4/1993 |
| EP | 0 563 720 | 10/1993 |
| EP | 0 568 389 | 11/1993 |
| EP | 0 582 201 | 2/1994 |
| EP | 0 916 624 | 5/1999 |
| EP | 0 919 551 | 6/1999 |
| EP | 1 059 278 | 12/2000 |
| EP | 1 106 237 | 6/2001 |
| EP | 1 153 887 | 11/2001 |
| EP | 1 163 946 | 12/2001 |
| EP | 1 298 154 | 4/2003 |
| EP | 0 561 441 | 9/2003 |
| EP | 1 411 027 | 4/2004 |
| EP | 1 752 435 | 2/2007 |
| EP | 1 752 436 | 2/2007 |
| EP | 1 760 060 | 3/2007 |
| EP | 1 762 556 | 3/2007 |
| EP | 1 770 081 | 4/2007 |
| EP | 1 772 446 | 4/2007 |
| EP | 1 775 278 | 4/2007 |
| EP | 2 085 364 | 8/2009 |
| FR | 1 476 073 | 4/1966 |
| FR | 2 565 229 | 12/1985 |
| FR | 2 752 242 | 2/1998 |
| FR | 2 862 644 | 5/2005 |
| FR | 2 868 419 | 10/2005 |
| FR | 2 869 612 | 11/2005 |
| FR | 2 869 613 | 11/2005 |
| FR | 2 872 504 | 1/2006 |
| FR | 2 881 732 | 8/2006 |
| FR | 2 885 903 | 11/2006 |
| FR | 2 912 743 | 8/2008 |
| FR | 2 913 683 | 9/2008 |
| FR | 2 918 058 | 1/2009 |
| FR | 2 925 045 | 6/2009 |
| FR | 2 929 611 | 10/2009 |
| FR | 2 935 699 | 3/2010 |
| FR | 2 935 968 | 3/2010 |
| GB | 14 767 | 1/1914 |
| GB | 404 938 | 7/1932 |
| GB | 406345 | 8/1932 |
| GB | 467 481 | 9/1935 |
| GB | 541357 | 11/1941 |
| GB | 679 536 | 9/1952 |
| GB | 736641 | 7/1953 |

| | | |
|---|---|---|
| GB | 799 567 | 8/1958 |
| GB | 1083594 | 11/1964 |
| GB | 984446 | 2/1965 |
| GB | 984 633 | 3/1965 |
| GB | 1 387 668 | 3/1972 |
| GB | 1286893 | 8/1972 |
| GB | 1 414 976 | 11/1975 |
| GB | 2 173 496 | 10/1986 |
| GB | 702143 | 10/1990 |
| GB | 2 336 584 | 10/1999 |
| JP | 39-27230 | 11/1928 |
| JP | 55-041858 | 3/1980 |
| JP | 56-29572 | 3/1981 |
| JP | 56-99432 | 8/1981 |
| JP | 61-112066 | 5/1986 |
| JP | 62-242638 | 10/1987 |
| JP | 63-195288 | 8/1988 |
| JP | 03-014527 | 1/1991 |
| JP | 03-223267 | 10/1991 |
| JP | 3-223267 | 10/1991 |
| JP | 04-089440 | 3/1992 |
| JP | 5213777 * | 8/1993 |
| JP | 6-25196 | 4/1994 |
| JP | 6-184024 | 7/1994 |
| JP | 06-321852 | 11/1994 |
| JP | 8-59593 | 3/1996 |
| JP | 09-299953 | 11/1997 |
| JP | 10-139700 | 5/1998 |
| JP | 10-218810 | 8/1998 |
| JP | 2001-213827 | 8/2001 |
| JP | 2001-1261581 | 9/2001 |
| JP | 2002-02033 | 1/2002 |
| JP | 2002-038195 | 2/2002 |
| JP | 2002-363153 | 12/2002 |
| JP | 2003-81891 | 3/2003 |
| JP | 2003-89680 | 3/2003 |
| JP | 2005-007841 | 1/2005 |
| JP | 2005-097177 | 4/2005 |
| JP | 76021635 | 4/2005 |
| KR | 2003-29740 | 5/2003 |
| KR | 10-0514819 | 11/2004 |
| SU | 123153 | 1/1959 |
| WO | WO 96/07617 | 3/1996 |
| WO | WO 97/48667 | 12/1997 |
| WO | WO 98/37024 | 8/1998 |
| WO | WO 99/32397 | 7/1999 |
| WO | WO 01/86220 | 11/2001 |
| WO | WO 02/26672 | 4/2002 |
| WO | WO 03/064357 | 8/2003 |
| WO | WO 2005/021476 | 3/2005 |
| WO | WO 2005/054167 | 6/2005 |
| WO | WO 2005/097722 | 10/2005 |
| WO | WO 2005/115954 | 12/2005 |
| WO | WO 2005/116004 | 12/2005 |
| WO | WO 2006/020234 | 2/2006 |
| WO | WO 2006/100311 | 9/2006 |
| WO | WO 2006/100312 | 9/2006 |
| WO | WO 2006/100313 | 9/2006 |
| WO | WO 2006/100314 | 9/2006 |
| WO | WO 2006/100315 | 9/2006 |
| WO | WO 2006/100316 | 9/2006 |
| WO | WO 2006/100317 | 9/2006 |
| WO | WO 2006/100318 | 9/2006 |
| WO | WO 2006/100319 | 9/2006 |
| WO | WO 2006/100320 | 9/2006 |
| WO | WO 2006/106153 | 10/2006 |
| WO | WO 2006/106154 | 10/2006 |
| WO | WO 2006/106155 | 10/2006 |
| WO | WO 2007/005405 | 5/2007 |
| WO | WO 2007/054505 | 5/2007 |
| WO | WO 2007/144335 | 12/2007 |
| WO | WO 2008/101866 | 8/2008 |
| WO | WO 2008/107468 | 9/2008 |
| WO | WO 2008/110588 | 9/2008 |
| WO | WO 2008/145729 | 12/2008 |
| WO | WO 2008/152043 | 12/2008 |
| WO | WO 2008/152044 | 12/2008 |
| WO | WO 2008/152045 | 12/2008 |
| WO | WO 2009/000773 | 12/2008 |
| WO | WO 2009/016149 | 2/2009 |
| WO | WO 2009/043796 | 4/2009 |
| WO | WO 2009/077528 | 6/2009 |
| WO | WO 2009/095429 | 8/2009 |
| WO | WO 2009/121853 | 10/2009 |
| WO | WO 2010/029039 | 3/2010 |
| WO | WO 2010/029153 | 3/2010 |

PUBLICATIONS

Carre et al., "La Transformation Des Alcools Polyatomiques En Mono-Et En Polychlorhydrines Au Moyen Du Chlorure De Thionyle", Bull. Soc. Chim. FR., No. 49, pp. 1150-1154, 1931.
Fauconnier, "Preparation De L'Epichlorhydrine", Bull. Soc. Chim. FR., No. 50, pp. 212-214, 1888.
"Industrially Important Epdxides", Ullmann'S Encyclopedia of Industrial Chemistry, 5.ed, vol. A9, pp. 539-540, 1988.
Bonner et al., "The Composition of Constant Boiling Hydrochloric Acid At Pressures of 50 to 1220 Millimeters", Journal of American Chemical Society, vol. 52, pp. 633-635, 1930.
Muskopf et al., "Epoxy Resins",Ullmann's Encyclopedia of Industrial Chemistry, 5.ed, vol. A9, pp. 547-562, 1988.
U.S. Appl. No. 11/914,879, filed Nov. 19, 2007, Gilbeau.
U.S. Appl. No. 11/915,059, filed Nov. 20, 2007, Gilbeau, et al.
U.S. Appl. No. 11/915,067, filed Nov. 20, 2007, Krafft, et al.
U.S. Appl. No. 11/914,874, filed Nov. 19, 2007, Krafft, et al.
U.S. Appl. No. 11/914,862, filed Nov. 19, 2007, Gilbeau.
U.S. Appl. No. 11/914,856, filed Nov. 19, 2007, Krafft, et al.
U.S. Appl. No. 11/914,868, filed Nov. 19, 2007, Krafft.
U.S. Appl. No. 11/915,046, filed Nov. 20, 2007, Krafft, et al.
U.S. Appl. No. 11/914,891, filed Nov. 19, 2007, Krafft, et al.
U.S. Appl. No. 11/915,056, filed Nov. 20, 2007, Gilbeau.
U.S. Appl. No. 11/915,053, filed Nov. 20, 2007, Gilbeau.
U.S. Appl. No. 11/915,088, filed Nov. 20, 2007, Krafft, et al.
U.S. Appl. No. 60/560,676, filed Apr. 8, 2004.
U.S. Appl. No. 60/734,659, filed Nov. 8, 2005.
U.S. Appl. No. 60/734,627, filed Nov. 8, 2005.
U.S. Appl. No. 60/734,657, filed Nov. 8, 2005.
U.S. Appl. No. 60/734,658, filed Nov. 8, 2005.
U.S. Appl. No. 60/734,635, filed Nov. 8, 2005.
U.S. Appl. No. 60/734,634, filed Nov. 8, 2005.
U.S. Appl. No. 60/734,637, filed Nov. 8, 2005.
U.S. Appl. No. 60/734,636, filed Nov. 8, 2005.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007.
Perry's Chemical Engineers Handbook $7^{th}$ Ed. $11^{th}$ Section, 1997.
Perry's Chemical Engineers Handbook $7^{th}$ Ed. $13^{th}$ Section, 1997.
Perry's Chemical Engineers Handbook $7^{th}$ Ed. $15^{th}$ Section, 1997.
Ullmann Encyclopedia Industr. Chem. $5^{th}$ Ed., vol. A23, 1993 pp. 635-636.
Ullmann Encyclopedia Industr. Chem. $5^{th}$ Ed., vol. A13, 1989 pp. 289.
Ullmann Encyclopedia Industr. Chem. $5^{th}$ Ed., vol. A11, 1988 pp. 354-360.
U.S. Appl. No. 12/304,391, filed Dec. 11, 2008, Kraft, et al.
Jeffrey Lutje Spelberg, et al., A Tandem Enzyme Reaction to Produce Optically Active Halohydrins, Epoxides and Diols, Tetrahedron: Asymmetry, Elsevier Science Publishers, vol. 10, No. 15, pp. 2863-2870, 1999.
Oleoline, com, Glycerine Market report, Sep. 10, 2003, No. 62,.

Notification Under Act. No. 100/2001, Coll. As Amended by Act No. 93/2004, Coll. To the extent of Annex No. 4, (SPOLEK) Nov. 30, 2004.

Documentation Under Act No. 100/2001 Coll. As amended by Act No. 93/2004 Coll in the scope of appendix No. 4 (SPOLEK) Jan. 11, 2005.

K. Weissermel and H J. Arpe in Industrial Organic Chemistry, Third, Completely Revised Edition, VCH, 1997, pp. 149,275.

Industrial Bioproducts: "Today and Tomorrow," Energetics, Inc. For the U.S. Department of Energy, Office of Energy Efficiency and Renewable Energy, Office of the Biomass Program, Jul. 2003, pp. 49, 52 to 56.

Kirk Othmer Encyclopedia of Chemical Technology, Fourth Edition, 1992, vol. 2, p. 156, John Wiley & sons, Inc.

Ullmann's Encyclopedia of Industrial Chemistry, Fifth, Completely Revised Edition, 1985, vol. A13, pp. 292-293.

The Merck Index, Eleventh Edition, 1989, pp. 759-760.

Ullmann's Encyclopedia of Industrial Chemistry, Fifth Completely Revised Edition, vol. A1, pp. 427-429, 1985.

Ullmann's Encyclopedia of Industrial Chemistry, Fifth Completely REvised Edition, vol. A6, pp. 240-252, 1985.

Hancock, E.G., Propylene and its Industrial Derivatives, 1973, pp. 298-332.

K. Weissermel and H. J. Arpe in Industrial Organic Chemistry, Third, Completely Revised Edition, VCH 1997, pp. 149-163.

K. Weissermel and H. J. Arpe in Industrial Organic Chemistry, Third, Completely Revised Edition, VCH 1997, pp. 275- 276.

Ullmann's Encyclopedia of Industrial Chemistry, Fifth Completely Revised Edition, vol. A9, pp. 539-540.

Perry's Chemical Engineers Handbook, Sixth Edition, Robert H. Perry, Don Green, 1984, Section 21-44 to 21-68.

Iwanami Dictionary of Physics and Chemistry, Third edition, Ryo Midorikawa/Iwanami Shoten, Publishers, May 29, 1971, pp. 270-271, 595 and 726.

Expert Opinion on the Environment Impact Assessment Documentation Pursuant to Annex No. 5 of Act No. 100/2001 Coll,. as amended by later regulations of the project/intent combined process for the manufacture of epichlorohydrin (SPOLEK) Apr. 2005.

Semendyava, N.D. et al., Khimicheskaya Promyshlennost, Seriya: Khornaya Promyshlennost (1981), 5, 21-2 (CA Summary) XP 002465275.

Rudnenko, E.V., et al., Kakokrasochnye Materialy I lkh Primenenie (1988), 4, 69-71 (CA Summary) XP 002465276.

Kirk Othmer Encyclopedia of Chemical Technology, Third Edition, vol. 12, 1980, pp. 1002-1005.

Chemical Engineering Handbook, the $6^{th}$ Edition, Edited by the Chemical Engineers, published by Maruzen Co., Ltd., 1999, pp. 1296-1306 w/English translation of p. 1296, Table 28.4, p. 1298, left column, lines 4-13 and p. 1305, Table 28.10.

Product Brouchure of De Dietrich Company, Apr. 1996, pp. 3, 8 and 9 w/English translation of p. 8, left column, lines 1-4, p. 9.

The Journal of the American Chemical Society, vol. XLV, Jul.-Dec. 1923, pp. 2771-2772.

Berichte Der Deutschen Chemischen Gesellschaft, 1891, vol. 24, pp. 508-510.

Myszkowski J. et al., "Removal of Chlorinated Organic Impurities from Hydrogen Chloride," CA, Jan. 1, 1900, XP002352444 (English CA Summary only).

Myszkowski J. et al., "Removal of Organic Compoiunds from Gaseous Hydrogen Chloride by an Absorption Method," CA, Jan. 1, 1900, XP002352445 (English CA summary only).

Milchert E. et al., "Recovering Hydrogen Chloride and Organic Chlor Compounds from the Reaction Mixture in the Chlorination of Ethylene," CA, Jan. 1, 1900, XP002352443 (English CA summary only).

Laine D.F., et al., "The Destruction of Organic Pollutants Under Mild Reaction Conditions ; A Review, " Microchemical Journal, vol. 85, No. 2, 2006, pp. 183-193.

Rainwater Harvesting and Utilization, Internet Citation, XP003003726.

H. Galeman, Organic Synthesis, Section 1, pp. 234-235.

Chemical Encyclopedia 5, p. 457.

Epoxy Resins, Shanghai Resin Plant, Shangai People's Press, 1971.

Martinetti Richard et al., "Environment Le Recyclage De l'eau," Industrie Textile, Ste. Sippe Sarl, Metz, FR., No. 1300, Jul. 1, 1998, ISSN: 0019-9176.

E. Milchert et al., "Installation for the Recovery of Dichloropropanols and Epichlorohydrin from the Waste Water in Epichlorohydrin Production", Pol. J. Appl. Chem., vol. 41, p. 113-118 (1997).

Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte- und Wassermengenwirtschaft e; V; - 2005 p. 81/-8/5., vol. 5.

Klaus Weissermel, et al., "Industrial Organic Chemistry," ($3^{rd}$ Completely Revised Edition); VCH 1997. p. 93-98.

Klaus Weissermel, et al., "Industrial Organic Chemistry," ($3^{rd}$ Completely Revised Edition); VCH 1997. p. 276-277.

Klaus Weissermel, et al., "Industrial Organic Chemistry," ($3^{rd}$ Completely Revised Edition); VCH 1997. p. 347-355.

U.S. Appl. No. 12/502,296, filed Jul. 14, 2009, Krafft, et al.

U.S. Appl. No. 12/502,342, filed Jul. 14, 2009, Krafft, et al.

U.S. Appl. No. 12/527,538, filed Aug. 17, 2009, Gilbeau, et al.

U.S. Appl. No. 12/529,777, filed Sep. 3, 2009, Krafft, et al.

U.S. Appl. No. 12/529,778, filed Sep. 3, 2009, Krafft, et al.

Catalogue of Nittetu Chemical Engineering Ltd. (Published in Mar. 1994).

12093 Chemicals, Chemical Daily Co., Ltd. (Published on Jan. 22, 1993) with attached English translation of relevant excerpts.

Chemicals Guide, Chemical Daily Co., Ltd. (Published on Jun. 15, 1990) with attached English translation of relevant excerpts.

Robert T. Morrison & Robert N. Boyd, Organic Chemistry, vol. II, pp. 666 to 667 and 712 to 714 (Japanese translation), published on Jul. 10, 1970, Tokyo Kagaku Dozin Co., Ltd. (and similar passages but retrieved from the English $5^{th}$ Edition of the Book, 1987.

U.S. Appl. No. 12/681,083, filed Mar. 31, 2010, Bobet, et al.

M. Schellentrager, "Untersuchungen zur oxidation Entfarbung aus gewahlter Reaktivfarbstoffe: Analyse der Abbauprodukte miteels hochauflosender LC-MS", Diisertation, XP002548413 (Jan. 1, 2006) w/Attached English Abstract.

U.S. Appl. No. 12/600,018, filed Nov. 13, 2009, Borremans, et al.

Medium and Long-Term Opportunities and Risks of the Biotechnologial Production of Bulk Chemicals from Renewable Resources—The Potential of White Biotechnology—The BREW Project—Final Report—Prepared under the European Commission's GRXTH Programme (DG Research) Utrecht, Sep. 2006 (pp. 29-31).

Ullmann Encyl. Indust. Chem., $5^{th}$ Ed., vol. A6, (1988), pp. 401-477.

Polymer Science Dictionary, M.S.M., Elsevier Applied Chemistry, London and New York 1989, p. 86.

Perry's chemical Engineers' Handbook, Sixth Edition, Section 21, pp. 21-55, 1973.

Ying Ling Liu, "Epoxy Resins from Novel Monomers with a Bis-(9,10-dihydro-9-oxa-10-oxide-10-phosphaphenanthrene-10- yl-) Substituent," Journal of Polymer Science: Part A: Polymer Chemistry, vol. 40, 359-368 (2002).

Ying Ling Liu, "Phosphorous-Containing Epoxy Resins from a Novel Synthesis Route," Journal of Applied Polymer Science, vol. 83, 1697-1701 (2002).

U.S. Appl. No. 12/663,753, filed Dec. 9, 2009, Krafft, et al.

U.S. Appl. No. 12/663,744, filed Dec. 9, 2009, Boulos, et al.

U.S. Appl. No. 12/663,749, filed Dec. 9, 2009, Krafft, et al.

U.S. Appl. No. 12/663,887, filed Dec. 10, 2009, Krafft, et al.

Fauconnier, "Preparation of Epichlorohydrin," Bull. Soc. Chim. Fr., No. 122, pp. 212-214 (With English Translation), 1989.

U.S. Appl. No. 12/745,802, filed Jun. 2, 2010, Gilbeau, et al.

H. Gilman, Organic Synthesis, Section 1, pp. 234-235, (1941).

Rainwater Harvesting and Utilization, Internet Citation, XP003003726, (Jan. 1, 2006).

Chemical Encyclopedia 5, p. 457, (1966).

Ullmann's Encyclopedia of Industrial Chemistry, 2005, Wiley-VCH GmbH & Co., KgaA, Weinhem, pp. 8-15 and 401-477, Published online Mar. 15, 2001.

U.S. Appl. No. 12/864,211, filed Jul. 27, 2010, Gilbeau, et al.

Armando Novelli, "The Preparation of Moni- and Dichlorohydrins of Glycerol," Anal. Farm. Bioquim, vol. 1, 1930, pp. 8-19 (with English Abstract).

Derwent Publications, An 109:6092 CA, JP 62-242638 (Oct. 23, 1987).

Derwent Publications, An 1987-338139 [48], JP 62-242638, (Oct. 23, 1987).

Kirk-Othmer Encyclopedia of Chemical Technology, Third Edition, vol. 4, Blood, Coagulants and Anticoagulants to Cardiovascular Agents, 1978.

J.B. Conant et al.. "Glycerol a,y-Dichlorophydrin," Organic Syntheses Coll., vol. 1, p. 292, 1941.

I. Miyakawa et al., Nagoya Sangyo Kagaku Kenkyusho Kenkyu Hokoku, 10, 49-52 (1957).

Han Xiu-Ying et al., Shanxi Daxue Xueba Bianjibu, 2002, 25(4), 379-80).

Herman A. Brunson, et al., "Thermal Decomposition of Glyceryl," Journal of the American CHemical Society, vol. 74, Apr. 1952 pp. 2100-2101.

* cited by examiner

METHOD FOR MAKING A CHLOROHYDRIN

This application is a 371 of PCT/EP2006/062439 filed May 19, 2006.

The present patent application claims the benefit of patent application FR 05.05120 and of patent application EP 05104321.4, both filed on 20 May 2005, and of provisional U.S. patent applications 60/734,659, 60/734,627, 60/734,657, 60/734,658, 60/734,635, 60/734,634, 60/734,637 and 60/734,636, all filed on 8 Nov. 2005, the content of all of which is incorporated here by reference.

The present invention relates to a process for preparing a chlorohydrin.

Chlorohydrins are reaction intermediates in the preparation of epoxides. Dichloropropanol, for example, is a reaction intermediate in the preparation of epichlorohydrin and of epoxy resins (Kirk-Othmer Encyclopedia of Chemical Technology, Fourth Edition, 1992, Vol. 2, page 156, John Wiley & Sons, Inc.).

According to known processes it is possible to obtain dichloropropanol in particular by hypochlorinating allyl chloride, by chlorinating allyl alcohol and by hydrochlorinating glycerol. This latter process has the advantage that the dichloropropanol can be obtained starting from fossil raw materials or from renewable raw materials, and it is known that natural petrochemical resources, from which the fossil materials are obtained, such as petroleum, natural gas or coal, for example, are limited in their terrestrial availability.

International application WO 2005/021476 describes a process for preparing dichloropropanol by reacting glycerol with gaseous hydrogen chloride in the presence of acetic acid as catalyst. The dichloropropanol is separated off by distillation. Application WO 2005/054167 of SOLVAY SA describes a process for preparing dichloropropanol by reacting glycerol with hydrogen chloride in the presence of an acid such as adipic acid as catalyst. The dichloropropanol is again separated off by distillation. In both processes the presence of dichloropropanol esters does not make it possible to optimize the step of separating the dichloropropanol and the other constituents of the reaction mixture.

The aim of the invention is to provide a process for preparing a chlorohydrin that does not exhibit these drawbacks.

The invention accordingly provides a process for preparing a chlorohydrin, comprising the following steps:

(a) a polyhydroxylated aliphatic hydrocarbon, an ester of a polyhydroxylated aliphatic hydrocarbon or a mixture thereof is reacted with a chlorinating agent and an organic acid so as to give a mixture containing the chlorohydrin and esters of the chlorohydrin (b) at least part of the mixture obtained in step (a) is subjected to one or more treatments in steps subsequent to step (a)

(c) polyhydroxylated aliphatic hydrocarbon is added to at least one of the steps subsequent to step (a), so as to react, at a temperature greater than or equal to 20° C., with the esters of the chlorohydrin, so as to form, at least partly, esters of the polyhydroxylated aliphatic hydrocarbon.

It has been found that the addition of the polyhydroxylated aliphatic hydrocarbon to step (c), subsequent to the transesterification reaction between the polyhydroxylated aliphatic hydrocarbon and the esters of the chlorohydrin, exhibits the following advantages, among others:

1) an increase in the yield of the separation process subsequent to the formation of an additional amount of the chlorohydrin 2) a reduction in the losses of catalyst present in step (a) of the process according to the invention, when the organic acid catalyzes the reaction of step (a)

3) a reduction of the losses of chlorinating agent optionally present in the mixture obtained in step (a).

The term "polyhydroxylated aliphatic hydrocarbon" refers to a hydrocarbon which contains at least two hydroxyl groups attached to two different saturated carbon atoms. The polyhydroxylated aliphatic hydrocarbon may contain, but is not limited to, from 2 to 60 carbon atoms.

Each of the carbons of a polyhydroxylated aliphatic hydrocarbon bearing the hydroxyl functional group (OH) cannot possess more than one OH group and must have sp3 hybridization. The carbon atom carrying the OH group may be primary, secondary or tertiary. The polyhydroxylated aliphatic hydrocarbon used in the present invention must contain at least two sp3-hybridized carbon atoms carrying an OH group. The polyhydroxylated aliphatic hydrocarbon includes any hydrocarbon containing a vicinal diol (1,2-diol) or a vicinal triol (1,2,3-triol), including the higher, vicinal or contiguous orders of these repeating units. The definition of the polyhydroxylated aliphatic hydrocarbon also includes, for example, one or more 1,3-, 1,4-, 1,5- and 1,6-diol functional groups. The polyhydroxylated aliphatic hydrocarbon may also be a polymer such as polyvinyl alcohol. Geminal diols, for example, are excluded from this class of polyhydroxylated aliphatic hydrocarbons.

The polyhydroxylated aliphatic hydrocarbons may contain aromatic moieties or heteroatoms, including, for example, heteroatoms of halogen, sulphur, phosphorus, nitrogen, oxygen, silicon and boron type, and mixtures thereof.

Polyhydroxylated aliphatic hydrocarbons which can be used in the present invention comprise, for example, 1,2-ethanediol (ethylene glycol), 1,2-propanediol (propylene glycol), 1,3-propanediol, 1-chloro-2,3-propanediol (chloropropanediol), 2-chloro-1,3-propanediol (chloropropanediol), 1,4-butanediol, 1,5-pentanediol, cyclohexanediols, 1,2-butanediol, 1,2-cyclohexanedimethanol, 1,2,3-propanetriol (also known as "glycerol" or "glycerin"), and mixtures thereof. With preference the polyhydroxylated aliphatic hydrocarbon used in the present invention includes, for example, 1,2-ethanediol, 1,2-propanediol, 1,3-propanediol, chloropropanediol and 1,2,3-propanetriol, and mixtures of at least two thereof. More preferably the polyhydroxylated aliphatic hydrocarbon used in the present invention includes, for example, 1,2-ethanediol, 1,2-propanediol, chloropropanediol and 1,2,3-propanetriol, and mixtures of at least two thereof. 1,2,3-Propanetriol or glycerol is the most preferred.

The esters of the polyhydroxylated aliphatic hydrocarbon may be present in the polyhydroxylated aliphatic hydrocarbon and/or may be produced in the process for preparing the chlorohydrin and/or may be prepared prior to the process for preparing the chlorohydrin. Examples of esters of the polyhydroxylated aliphatic hydrocarbon comprise ethylene glycol monoacetate, propanediol monoacetates, glycerol monoacetates, glycerol monostearates, glycerol diacetates and mixtures thereof.

The term "chlorohydrin" is used here in order to describe a compound containing at least one hydroxyl group and at least one chlorine atom attached to different saturated carbon atoms. A chlorohydrin which contains at least two hydroxyl groups is also a polyhydroxylated aliphatic hydrocarbon. Accordingly the starting material and the product of the reaction may each be chlorohydrins. In that case the "product" chlorohydrin is more chlorinated than the starting chlorohydrin, in other words has more chlorine atoms and fewer hydroxyl groups than the starting chlorohydrin. Preferred chlorohydrins are chloroethanol, chloropropanol, chloropropanediol, dichloropropanol and mixtures of at least two thereof. Dichloropropanol is particularly preferred. Chlorohydrins which are more particularly preferred are 2-chloroethanol, 1-chloropropan-2-ol, 2-chloropropan-1-ol, 1-chloropropane-2,3-diol, 2-chloropropane-1,3-diol, 1,3-dichloropropan-2-ol, 2,3-dichloropropan-1-ol and mixtures of at least two thereof.

The polyhydroxylated aliphatic hydrocarbon, the ester of polyhydroxylated aliphatic hydrocarbon, or the mixture thereof in the process according to the invention may be obtained starting from fossil raw materials or starting from renewable raw materials, preferably starting from renewable raw materials.

By fossil raw materials are meant materials obtained from the processing of petrochemical natural resources, such as petroleum, natural gas and coal, for example. Among these materials preference is given to organic compounds containing 2 and 3 carbon atoms. When the polyhydroxylated aliphatic hydrocarbon is glycerol, allyl chloride, allyl alcohol and "synthetic" glycerol are particularly preferred. By "synthetic" glycerol is meant a glycerol generally obtained from petrochemical resources. When the polyhydroxylated aliphatic hydrocarbon is ethylene glycol, ethylene and "synthetic" ethylene glycol are particularly preferred. By "synthetic" ethylene glycol is meant an ethylene glycol generally obtained from petrochemical resources. When the polyhydroxylated aliphatic hydrocarbon is propylene glycol, propylene and "synthetic" propylene glycol are particularly preferred. By "synthetic" propylene glycol is meant a propylene glycol generally obtained from petrochemical resources.

By renewable raw materials are meant materials obtained from the processing of renewable natural resources. Among these materials preference is given to "natural" ethylene glycol, "natural" propylene glycol and "natural" glycerol. "Natural" ethylene glycol, propylene glycol and glycerol are obtained for example by conversion of sugars by thermochemical processes, it being possible for these sugars to be obtained starting from biomass, as described in "Industrial Bioproducts: Today and Tomorrow", Energetics, Incorporated for the U.S. Department of Energy, Office of Energy Efficiency and Renewable Energy, Office of the Biomass Program, July 2003, pages 49, 52 to 56. One of these processes is, for example, the catalytic hydrogenolysis of sorbitol obtained by thermochemical conversion of glucose. Another process is, for example, the catalytic hydrogenolysis of xylitol obtained by hydrogenation of xylose. The xylose may for example be obtained by hydrolysis of the hemicellulose present in maize fibres. By "natural glycerol" or "glycerol obtained from renewable raw materials" is meant, in particular, glycerol obtained during the production of biodiesel or else glycerol obtained during conversions of animal or vegetable oils or fats in general, such as saponification, transesterification or hydrolysis reactions.

Among the oils which can be used to prepare natural glycerol, mention may be made of all common oils, such as palm oil, palm kernel oil, copra oil, babassu oil, former or new (low erucic acid) colza oil, sunflower oil, maize oil, castor oil and cotton oil, peanut oil, soya bean oil, linseed oil and crambe oil, and all oils obtained, for example, from sunflower plants or colza plants obtained by genetic modification or hybridization.

It is also possible to employ used frying oils, various animal oils, such as fish oils, tallow, lard and even squaring greases.

Among the oils used mention may also be made of oils which have been partly modified by means, for example, of polymerization or oligomerization, such as, for example, the "stand oils" of linseed oil and of sunflower oil, and blown vegetable oils.

A particularly suitable glycerol may be obtained during the conversion of animal fats. Another particularly suitable glycerol may be obtained during the production of biodiesel. A third, very suitable glycerol may be obtained during the conversion of animal or vegetable oils or fats by transesterification in the presence of a heterogeneous catalyst, as described in documents FR 2752242, FR 2869612 and FR 2869613. More specifically, the heterogeneous catalyst is selected from mixed oxides of aluminium and zinc, mixed oxides of zinc and titanium, mixed oxides of zinc, titanium and aluminium, and mixed oxides of bismuth and aluminium, and the heterogeneous catalyst is employed in the form of a fixed bed. This latter process can be a process for producing biodiesel.

In the process for preparing a chlorohydrin according to the invention, the polyhydroxylated aliphatic hydrocarbon may be as described in the patent application entitled "Process for preparing chlorohydrin by converting polyhydroxylated aliphatic hydrocarbons", filed in the name of SOLVAY SA on the same day as the present application, and the content of which is incorporated here by reference.

Particular mention is made of a process for preparing a chlorohydrin wherein a polyhydroxylated aliphatic hydrocarbon, an ester of a polyhydroxylated aliphatic hydrocarbon or a mixture thereof whose total metal content, expressed in elemental form, is greater than or equal to 0.1 µg/kg and less than or equal to 1000 mg/kg is reacted with a chlorinating agent.

In the process according to the invention it is preferred to use glycerol obtained starting from renewable raw materials.

In the process for preparing a chlorohydrin according to the invention, the polyhydroxylated aliphatic hydrocarbon, the ester of polyhydroxylated aliphatic hydrocarbon or the mixture thereof may be a crude product or a purified product, such as are specifically disclosed in application WO 2005/054167 of SOLVAY SA, from page 2 line 8 to page 4 line 2.

In the process for preparing a chlorohydrin according to the invention, the polyhydroxylated aliphatic hydrocarbon, the ester of polyhydroxylated aliphatic hydrocarbon or the mixture thereof may have an alkali metal and/or alkaline earth metal content of less than or equal to 5 g/kg, as described in the application entitled "Process for preparing a chlorohydrin by chlorinating a polyhydroxylated aliphatic hydrocarbon", filed in the name of SOLVAY SA on the same day as the present application, and whose content is incorporated here by reference. The alkali metals may be selected from lithium, sodium, potassium, rubidium and cesium and the alkaline earth metals may be selected from magnesium, calcium, strontium and barium.

In the process according to the invention, the alkali metal and/or alkaline earth metal content of the polyhydroxylated aliphatic hydrocarbon, the ester of polyhydroxylated aliphatic hydrocarbon or the mixture thereof is less than or equal to 5 g/kg, often less than or equal to 1 g/kg, more particularly less than or equal to 0.5 g/kg and in certain cases less than or equal to 0.01 g/kg. The alkali metal and/or alkaline earth metal content of the glycerol is generally greater than or equal to 0.1 µg/kg.

In the process according to the invention the alkali metals are generally lithium, sodium, potassium and cesium, often sodium and potassium, and frequently sodium.

In the process for preparing a chlorohydrin according to the invention, the lithium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 µg/kg.

In the process according to the invention, the sodium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 μg/kg.

In the process according to the invention, the potassium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.11 g/kg.

In the process according to the invention, the rubidium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 μg/kg.

In the process according to the invention, the cesium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 μg/kg.

In the process according to the invention the alkaline earth metal elements are generally magnesium, calcium, strontium and barium, often magnesium and calcium and frequently calcium.

In the process according to the invention, the magnesium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 μg/kg.

In the process according to the invention, the calcium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 μg/kg.

In the process according to the invention, the strontium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 μg/kg.

In the process according to the invention, the barium content of the polyhydroxylated aliphatic hydrocarbon, the ester of polyhydroxylated aliphatic hydrocarbon or the mixture thereof is generally less than or equal to 1 g/kg, often less than or equal to 0.1 g/kg and more particularly less than or equal to 2 mg/kg. This content is generally greater than or equal to 0.1 μg/kg.

In the process according to the invention the alkali and/or alkaline earth metals are generally present in the form of salts, frequently in the form of chlorides, sulphates and mixtures thereof. Sodium chloride is the most often encountered.

In the process for preparing a chlorohydrin according to the invention, the chlorinating agent may be as described in application WO 2005/054167 of SOLVAY SA, from page 4 line 25 to page 6 line 2.

In the process for preparing a chlorohydrin according to the invention, the chlorinating agent may be hydrogen chloride as described in application WO 2005/054167 of SOLVAY SA, from page 4 line 30 to page 6 line 2.

Particular mention is made of a chlorinating agent, which may be aqueous hydrochloric acid or hydrogen chloride which is preferably anhydrous. The hydrogen chloride may originate from a process of pyrolysing organic chlorine compounds, such as, for example, from vinyl chloride preparation, from a process for preparing 4,4-methylenediphenyl diisocyanate (MDI) or toluene diisocyanate (TDI), from metal pickling processes or from the reaction of an inorganic acid such as sulphuric or phosphoric acid with a metal chloride such as sodium chloride, potassium chloride or calcium chloride.

In one advantageous embodiment of the process for preparing a chlorohydrin according to the invention, the chlorinating agent is gaseous hydrogen chloride or an aqueous solution of hydrogen chloride, or a combination of the two.

In the process for preparing a chlorohydrin according to the invention, the hydrogen chloride may be an aqueous solution of hydrogen chloride or of the hydrogen chloride, preferably anhydrous, obtained from plant for preparing allyl chloride and/or for preparing chloromethanes and/or for chlorinolysis and/or for high-temperature oxidation of chlorine compounds, as described in the application entitled "Process for preparing a chlorohydrin by reacting a polyhydroxylated aliphatic hydrocarbon with a chlorinating agent", filed in the name of SOLVAY SA on the same day as the present application, and the content of which is incorporated here by reference.

Particular mention is made of a process for preparing a chlorohydrin from a polyhydroxylated aliphatic hydrocarbon, from an ester of a polyhydroxylated aliphatic hydrocarbon or from a mixture thereof, and from a chlorinating agent, the chlorinating agent comprising at least one of the following compounds: nitrogen, oxygen, hydrogen, chlorine, an organic hydrocarbon compound, an organic halogen compound, an organic oxygen compound and a metal.

Particular mention is made of an organic hydrocarbon compound selected from saturated and unsaturated aliphatic and aromatic hydrocarbons and mixtures thereof.

Particular mention is made of an unsaturated aliphatic hydrocarbon selected from acetylene, ethylene, propylene, butene, propadiene, methylacetylene and mixtures thereof, of a saturated aliphatic hydrocarbon selected from methane, ethane, propane, butane and mixtures thereof and of an aromatic hydrocarbon which is benzene.

Particular mention is made of an organic halogen compound which is an organic chlorine compound selected from chloromethanes, chloroethanes, chloropropanes, chlorobutanes, vinyl chloride, vinylidene chloride, monochloropropenes, perchloroethylene, trichloroethylene, chlorobutadienes, chlorobenzenes and mixtures thereof.

Particular mention is made of an organic halogen compound which is an organic fluorine compound selected from fluoromethanes, fluoroethanes, vinyl fluoride, vinylidene fluoride and mixtures thereof.

Particular mention is made of an organic oxygen compound selected from alcohols, chloroalcohols, chloroethers and mixtures thereof.

Particular mention is made of a metal selected from alkali metals, alkaline earth metals, iron, nickel, copper, lead, arsenic, cobalt, titanium, cadmium, antimony, mercury, zinc, selenium, aluminium, bismuth and mixtures thereof.

Mention is made more particularly of a process wherein the chlorinating agent is obtained at least partly from a process for preparing allyl chloride and/or a process for preparing chloromethanes and/or a process of chlorinolysis and/or a process for oxidizing chlorine compounds at a temperature greater than or equal to 800° C.

In one advantageous embodiment of the process for preparing a chlorohydrin according to the invention, the hydrogen chloride is an aqueous solution of hydrogen chloride, and does not content gaseous hydrogen chloride.

In the process for preparing a chlorohydrin according to the invention, the reaction of the polyhydroxylated aliphatic hydrocarbon, the ester of polyhydroxylated aliphatic hydrocarbon or the mixture thereof with the chlorinating agent may be carried out in a reactor as described in application WO 2005/054167 of SOLVAY SA on page 6 lines 3 to 23.

Mention is made particularly of plant made of or covered with materials which are resistant, under the conditions of the reaction, to the chlorinating agents, in particular to hydrogen chloride. Mention is made more particularly of plant made of enamelled steel or of tantalum.

In the process for preparing a chlorohydrin according to the invention, the reaction of the polyhydroxylated aliphatic hydrocarbon, the ester of the polyhydroxylated aliphatic hydrocarbon or the mixture thereof with the chlorinating agent may be carried out in apparatus which is made of or covered with materials that are resistant to chlorinating agents, as described in the patent application entitled "Process for preparing a chlorohydrin in corrosion-resistant apparatus", filed in the name of SOLVAY SA on the same day as the present application, and the content of which is incorporated here by reference.

Particular mention is made of a process for preparing a chlorohydrin that includes a step in which a polyhydroxylated aliphatic hydrocarbon, an ester of a polyhydroxylated aliphatic hydrocarbon or a mixture thereof is subjected to reaction with a chlorinating agent containing hydrogen chloride and to at least one other step carried out in an apparatus made of or covered with materials resistant to the chlorinating agent, under the conditions in which that step is realized. Mention is made more particularly of metallic materials such as enamelled steel, gold and tantalum and of non-metallic materials such as high-density polyethylene, polypropylene, poly(vinylidene fluoride), polytetrafluoroethylene, perfluoroalkoxyalkanes and poly(perfluoropropyl vinyl ether), polysulphones and polysulphides, and unimpregnated and impregnated graphite.

In the process for preparing a chlorohydrin according to the invention, the reaction of the polyhydroxylated aliphatic hydrocarbon, the ester of polyhydroxylated aliphatic hydrocarbon or the mixture thereof with the chlorinating agent may be carried out in a reaction medium as described in the application entitled "Continuous process for preparing chlorohydrins", filed in the name of SOLVAY SA on the same day as the present application, and the content of which is incorporated here by reference.

Particular mention is made of a continuous process for producing chlorohydrin in which a polyhydroxylated aliphatic hydrocarbon, an ester of a polyhydroxylated aliphatic hydrocarbon or a mixture thereof is reacted with a chlorinating agent and an organic acid in a liquid reaction medium whose steady-state composition comprises polyhydroxylated aliphatic hydrocarbon and esters of polyhydroxylated aliphatic hydrocarbon for which the sum of the amounts, expressed in moles of polyhydroxylated aliphatic hydrocarbon, is greater than 1.1 mol % and less than or equal to 30 mol %, the percentage being based on the organic part of the liquid reaction medium.

The organic part of the liquid reaction medium consists of all of the organic compounds of the liquid reaction medium, in other words the compounds whose molecule contains at least one carbon atom.

In the process for preparing a chlorohydrin according to the invention, the reaction of the polyhydroxylated aliphatic hydrocarbon, the ester of polyhydroxylated aliphatic hydrocarbon or the mixture thereof and the chlorinating agent may be carried out in the presence of a catalyst as described in application WO 2005/054167 of SOLVAY SA from page 6 line 28 to page 8 line 5.

Mention is made particularly of a catalyst based on a carboxylic acid or on a carboxylic acid derivative having an atmospheric boiling point of greater than or equal to 200° C., especially adipic acid and derivatives of adipic acid.

In the process for preparing a chlorohydrin according to the invention, the reaction of the polyhydroxylated aliphatic hydrocarbon, the ester of polyhydroxylated aliphatic hydrocarbon or the mixture thereof and the chlorinating agent may be carried out at a catalyst concentration, temperature and pressure and for residence times as described in the application WO 2005/054167 of SOLVAY SA from page 8 line 6 to page 10 line 10.

Mention is made particularly of a temperature of at least 20° C. and not more than 160° C., of a pressure of at least 0.3 bar and not more than 100 bar and of a residence time of at least 1 h and not more than 50 h.

In the process for preparing a chlorohydrin according to the invention, the reaction of the polyhydroxylated aliphatic hydrocarbon, the ester of polyhydroxylated aliphatic hydrocarbon or the mixture thereof with the chlorinating agent may be carried out in the presence of a solvent as described in application WO 2005/054167 of SOLVAY SA at page 11 lines 12 to 36.

Mention is made particularly of organic solvents such as a chlorinated organic solvent, an alcohol, a ketone, an ester or an ether, a non-aqueous solvent which is miscible with the polyhydroxylated aliphatic hydrocarbon, such as chloroethanol, chloropropanol, chloropropanediol, dichloropropanol, dioxane, phenol, cresol and mixtures of chloropropanediol and dichloropropanol, or heavy products of the reaction such as at least partially chlorinated and/or esterified oligomers of the polyhydroxylated aliphatic hydrocarbon.

In the process for preparing a chlorohydrin according to the invention, the reaction of the polyhydroxylated aliphatic hydrocarbon, the ester of polyhydroxylated aliphatic hydrocarbon or the mixture thereof with the chlorinating agent may be carried out in the presence of a liquid phase comprising heavy compounds other than the polyhydroxylated aliphatic hydrocarbon, as described in the application entitled "Process for preparing a chlorohydrin in a liquid phase", filed in the name of SOLVAY SA on the same day as the present application, and the content of which is incorporated here by reference.

Particular mention is made of a process for preparing a chlorohydrin wherein a polyhydroxylated aliphatic hydrocarbon, an ester of polyhydroxylated aliphatic hydrocarbon or a mixture thereof is subjected to reaction with a chlorinating agent in the presence of a liquid phase comprising heavy compounds other than the polyhydroxylated aliphatic hydrocarbon and having a boiling temperature under a pressure of 1 bar absolute of at least 15° C. more than the boiling temperature of the chlorohydrin under a pressure of 1 bar absolute.

In the process for preparing a chlorohydrin according to the invention the reaction of the polyhydroxylated aliphatic hydrocarbon, an ester of the polyhydroxylated aliphatic hydrocarbon or a mixture thereof with the chlorinating agent is preferably carried out in a liquid reaction medium. The liquid reaction medium may be a single-phase or multi-phase medium.

The liquid reaction medium is composed of all of the dissolved or dispersed solid compounds, dissolved or dispersed liquid compounds and dissolved or dispersed gaseous compounds at the temperature of the reaction.

The reaction medium comprises the reactants, the catalyst, the solvent, the impurities present in the reactants, in the solvent and in the catalyst, the reaction intermediates, the products and the by-products of the reaction.

By reactants are meant the polyhydroxylated aliphatic hydrocarbon, the ester of polyhydroxylated aliphatic hydrocarbon and the chlorinating agent.

Among the impurities present in the polyhydroxylated aliphatic hydrocarbon mention may be made of carboxylic acids, salts of carboxylic acids, esters of fatty acid with the polyhydroxylated aliphatic hydrocarbon, esters of fatty acids with the alcohols used in the transesterification, and inorganic salts such as alkali metal or alkaline earth metal sulphates and chlorides.

When the polyhydroxylated aliphatic hydrocarbon is glycerol, the impurities in the glycerol that may be mentioned include carboxylic acids, salts of carboxylic acids, fatty acid esters such as mono-, di- and triglycerides, esters of fatty acids with the alcohols used in the transesterification and inorganic salts such as alkali metal or alkaline earth metal sulphates and chlorides.

Among the reaction intermediates mention may be made of monochlorohydrins of the polyhydroxylated aliphatic hydrocarbon and their esters and/or polyesters, the esters and/or polyesters of the polyhydroxylated aliphatic hydrocarbon and the esters of polychlorohydrins.

When the chlorohydrin is dichloropropanol, the reaction intermediates that may be mentioned include glycerol monochlorohydrin and its esters and/or polyesters, the esters and/or polyesters of glycerol and the esters of dichloropropanol.

The ester of polyhydroxylated aliphatic hydrocarbon may therefore be, at each instance, a reactant, an impurity of the polyhydroxylated aliphatic hydrocarbon or a reaction intermediate.

By products of the reaction are meant the chlorohydrin and water. The water may be the water formed in the chlorination reaction and/or water introduced into the process, for example via the polyhydroxylated aliphatic hydrocarbon and/or the chlorinating agent, as described in the application WO 2005/054167 of SOLVAY SA at page 2 lines 22 to 28 to page 3 lines 20 to 25, at page 5 lines 7 to 31 and at page 12 lines 14 to 19.

Among the by-products mention may be made for example of the partially chlorinated and/or esterified oligomers of the polyhydroxylated aliphatic hydrocarbon.

When the polyhydroxylated aliphatic hydrocarbon is glycerol, the by-products that may be mentioned include, for example, the partially chlorinated and/or esterified oligomers of glycerol.

The reaction intermediates and the by-products may be formed in the different steps of the process, such as, for example, during the step of preparing the chlorohydrin and during the steps of separating off the chlorohydrin.

The liquid reaction mixture may therefore contain the polyhydroxylated aliphatic hydrocarbon, the chlorinating agent in solution or dispersion in the form of bubbles, the catalyst, the solvent, the impurities present in the reactants, in the solvent and in the catalyst, such as dissolved or solid salts, for example, the reaction intermediates, the products and the by-products of the reaction.

Steps (a), (b) and (c) of the process according to the invention may be carried out in batch mode or in continuous mode. Preference is given to carrying out all of the steps in continuous mode.

In the process according to the invention, the separation of the chlorohydrin and of the other compounds from the reaction mixture may be carried out in accordance with the methods as described in the application WO 2005/054167 of SOLVAY SA from page 12 line 1 to page 16 line 35 and page 18 lines 6 to 13. These other compounds are those mentioned above and include unconsumed reactants, the impurities present in the reactants, the catalyst, the solvent, the reaction intermediates, the water and the by-products of the reaction.

Particular mention is made of separation by azeotropic distillation of a water/chlorohydrin/chlorinating agent mixture under conditions which minimize the losses of chlorinating agent, followed by isolation of the chlorohydrin by phase separation.

In the process for preparing a chlorohydrin according to the invention, the isolation of the chlorohydrin and of the other compounds from the reaction mixture may be carried out in accordance with methods of the kind described in patent application EP 05104321.4, filed in the name of SOLVAY SA on 20/05/2005 and the content of which is incorporated here by reference. Particular mention is made of a separation method including at least one separating operation intended to remove the salt from the liquid phase.

Particular mention is made of a process for preparing a chlorohydrin by reacting a polyhydroxylated aliphatic hydrocarbon, an ester of a polyhydroxylated aliphatic hydrocarbon or a mixture thereof with a chlorinating agent wherein the polyhydroxylated aliphatic hydrocarbon, an ester of the polyhydroxylated aliphatic hydrocarbon or a mixture thereof that is used comprises at least one solid or dissolved metal salt, the process including a separation operation intended to remove part of the metal salt. Mention is made more particularly of a process for preparing a chlorohydrin by reacting a polyhydroxylated aliphatic hydrocarbon, an ester of a polyhydroxylated aliphatic hydrocarbon or a mixture thereof with a chlorinating agent wherein the polyhydroxylated aliphatic hydrocarbon, an ester of a polyhydroxylated aliphatic hydrocarbon or a mixture thereof that is used comprises at least one chloride and/or a sodium and/or potassium sulphate and in which the separating operation intended to remove part of the metal salt is a filtering operation. Particular mention is also made of a process for preparing a chlorohydrin wherein (a) a polyhydroxylated aliphatic hydrocarbon, an ester of a polyhydroxylated aliphatic hydrocarbon or a mixture thereof is subjected to reaction with a chlorinating agent in a reaction mixture, (b) continuously or periodically, a fraction of the reaction mixture containing at least water and the chlorohydrin is removed, (c) at least a part of the fraction obtained in step (b) is introduced into a distillation step and (d) the reflux ratio of the distillation step is controlled by providing water to the said distillation step. Mention is made very particularly of a process for preparing a chlorohydrin wherein (a) a polyhydroxylated aliphatic hydrocarbon, an ester of a polyhydroxylated aliphatic hydrocarbon or a mixture thereof is subjected to reaction with hydrogen chloride in a reaction mixture, (b) continuously or periodically, a fraction of the reaction mixture containing at least water and chlorohydrin is removed, (c) at least part of the fraction obtained in step (b) is introduced into a distillation step in which the ratio between the hydrogen chloride concentration and the water concentration in the fraction introduced into the distillation step is smaller than the hydrogen chloride/water concentration ratio in the binary azeotropic hydrogen chloride/water composition at the distillation temperature and pressure.

In the process for preparing a chlorohydrin according to the invention, the separation of the chlorohydrin and the other compounds from the reaction mixture from chlorination of the polyhydroxylated aliphatic hydrocarbon may be carried out in accordance with methods as described in the application entitled "Process for preparing a chlorohydrin starting from a polyhydroxylated aliphatic hydrocarbon", filed in the name of SOLVAY SA on the same day as the present application, and the content of which is incorporated here by reference.

Particular mention is made of a process for preparing chlorohydrin by reacting a polyhydroxylated aliphatic hydrocarbon, an ester of a polyhydroxylated aliphatic hydrocarbon or a mixture thereof with a chlorinating agent in a reactor which is supplied with one or more liquid streams containing less than 50% by weight of the polyhydroxylated aliphatic hydrocarbon, of the ester of polyhydroxylated aliphatic hydrocarbon or of the mixture thereof relative to the weight of the entirety of the liquid streams introduced into the reactor.

More particular mention is made of a process comprising the following steps: (a) a polyhydroxylated aliphatic hydrocarbon, an ester of a polyhydroxylated aliphatic hydrocarbon or a mixture thereof is reacted with a chlorinating agent so as to give at least one mixture containing the chlorohydrin, water and the chlorinating agent, (b) at least a fraction of the mixture formed in step (a) is removed, and (c) the fraction removed in step (b) is subjected to an operation of distillation and/or stripping wherein the polyhydroxylated aliphatic hydrocarbon is added in order to isolate, from the fraction removed in step (b), a mixture containing water and the chlorohydrin and exhibiting a reduced chlorinating agent content as compared with the fraction removed in step (b).

In the process for preparing a chlorohydrin according to the invention, the separation of the chlorohydrin and of the other compounds from the reaction mixture from chlorination of the polyhydroxylated aliphatic hydrocarbon may be carried out in accordance with methods as described in the application entitled "Process for converting polyhydroxylated aliphatic hydrocarbons into chlorohydrins", filed in the name of SOLVAY SA on the same day as the present application, and the content of which is incorporated here by reference. Particular mention is made of a process for preparing a chlorohydrin that comprises the following steps: (a) a polyhydroxylated aliphatic hydrocarbon, an ester of a polyhydroxylated aliphatic hydrocarbon or a mixture thereof is reacted with a chlorinating agent so as to give a mixture containing the chlorohydrin, chlorohydrin esters and water, (b) at least a fraction of the mixture obtained in step (a) is subjected to a distillation and/or stripping treatment so as to give a portion concentrated in water, in chlorohydrin and in chlorohydrin esters, and (c) at least a fraction of the portion obtained in step (b) is subjected to a separating operation in the presence of at least one additive so as to obtain a moiety concentrated in chlorohydrin and in chlorohydrin esters and containing less than 40% by weight of water.

The separating operation is more particularly a decantation.

In the process for preparing a chlorohydrin according to the invention, the isolation and the treatment of the other compounds of the reaction mixture may be carried out in accordance with methods as described in the application entitled "Process for preparing a chlorohydrin by chlorinating a polyhydroxylated aliphatic hydrocarbon", filed in the name of SOLVAY SA on the same day as the present application. A preferred treatment consists in subjecting a fraction of the by-products of the reaction to a high-temperature oxidation.

Particular mention is made of a process for preparing a chlorohydrin that comprises the following steps: (a) a polyhydroxylated aliphatic hydrocarbon, an ester of a polyhydroxylated aliphatic hydrocarbon or a mixture thereof whose alkali metal and/or alkaline earth metal content is less than or equal to 5 g/kg, an chlorinating agent and an organic acid are reacted so as to give a mixture containing at least the chlorohydrin and by-products, (b) at least a portion of the mixture obtained in step (a) is subjected to one or more treatments in steps subsequent to step (a), and (c) at least one of the steps subsequent to step (a) consists in an oxidation at a temperature greater than or equal to 800° C. More particular mention is made of a process wherein, in the subsequent step, a portion of the mixture obtained in step (a) is removed and this portion is subjected to oxidation at a temperature greater than or equal to 800° C. in the course of the removal. Particular mention is also made of a process wherein the treatment of step (b) is a separating operation selected from decantation, filtration, centrifugation, extraction, washing, evaporation, stripping, distillation, and adsorption operations or the combinations of at least two of these operations.

In the process according to the invention, when the chlorohydrin is chloropropanol, it is generally employed in the form of a mixture of compounds comprising the isomers of 1-chloropropan-2-ol and 2-chloropropan-1-ol. This mixture generally contains more than 1% by weight of the two isomers, preferably more than 5% by weight and particularly more than 50%. The mixture commonly contains less than 99.9% by weight of the two isomers, preferably less than 95% by weight and more particularly less than 90% by weight. The other constituents of the mixture may be compounds originating from the processes for preparing the chloropropanol, such as residual reactants, reaction by-products, solvents and, in particular, water.

The mass ratio of the isomers, 1-chloropropan-2-ol and 2-chloropropan-1-ol, is commonly greater than or equal to 0.01, preferably greater than or equal to 0.4. This ratio is commonly less than or equal to 99 and preferably less than or equal to 25.

In the process according to the invention, when the chlorohydrin is chloroethanol, it is generally employed in the form of a mixture of compounds comprising the 2-chloroethanol isomer. This mixture generally contains more than 1% by weight of the isomer, preferably more than 5% by weight and particularly more than 50%. The mixture commonly contains less than 99.9% by weight of the isomer, preferably less than 95% by weight and more particularly less than 90% by weight. The other constituents of the mixture may be compounds originating from the processes for preparing the chloroethanol, such as residual reactants, reaction by-products, solvents and, in particular, water.

In the process according to the invention, when the chlorohydrin is chloropropanediol, it is generally employed in the form of a mixture of compounds comprising the isomers of 1-chloropropane-2,3-diol and 2-chloropropane-1,3-diol. This mixture generally contains more than 1% by weight of the two isomers, preferably more than 5% by weight and particularly more than 50%. The mixture commonly contains less than 99.9% by weight of the two isomers, preferably less than 95% by weight and more particularly less than 90% by weight. The other constituents of the mixture may be compounds originating from the processes for preparing the chloropropanediol, such as residual reactions, reaction by-products, solvents and, in particular, water.

The mass ratio between the 1-chloropropane-2,3-diol and 2-chloropropane-1,3-diol isomers is commonly greater than or equal to 0.01, preferably greater than or equal to 0.4. This ratio is commonly less than or equal to 99 and preferably less than or equal to 25.

In the process according to the invention, when the chlorohydrin is dichloropropanol, it is generally employed in the form of a mixture of compounds comprising the isomers of 1,3-dichloropropan-2-ol and 2,3-dichloropropan-1-ol. This mixture generally contains more than 1% by weight of the two isomers, preferably more than 5% by weight and in particular more than 50%. The mixture commonly contains less than 99.9% by weight of the two isomers, preferably less than 95% by weight and more particularly less than 90% by weight. The other constituents of the mixture may be compounds originating from the processes for preparing the dichloropropanol, such as residual reactants, reaction by-products, solvents and, in particular, water.

The mass ratio between the 1,3-dichloropropan-2-ol and 2,3-dichloropropan-1-ol isomers is commonly greater than or equal to 0.01, often greater than or equal to 0.4, frequently greater than or equal to 1.5, preferably greater than or equal to 3.0, more preferably greater than or equal to 7.0 and with very particular preference greater than or equal to 20.0. This ratio is commonly less than or equal to 99 and preferably less than or equal to 25.

In the process for preparing a chlorohydrin according to the invention, the organic acid may be a product originating from the process for preparing the polyhydroxylated aliphatic hydrocarbon or a product not originating from this process. In this latter case the product in question may be an organic acid which is used in order to catalyse the reaction of the polyhydroxylated aliphatic hydrocarbon with the chlorinating agent. The organic acid may also be a mixture of an organic acid originating from the process for preparing the polyhydroxylated aliphatic hydrocarbon, and an organic acid not originating from the process for preparing the polyhydroxylated aliphatic hydrocarbon.

In the process according to the invention, the esters of the polyhydroxylated aliphatic hydrocarbon may originate from the reaction between the polyhydroxylated aliphatic hydrocarbon and the organic acid, before, during or within the steps which follow the reaction with the chlorinating agent.

In the process according to the invention, the esters of the chlorohydrin may originate from the reaction of the chlorohydrin with the organic acid in the course of the step of preparing the chlorohydrin. The organic acid is as defined above.

The amount of chlorohydrin in the mixture containing the chlorohydrin and esters of the chlorohydrin is generally greater than or equal to 2% by weight, often greater than or equal to 4% by weight and more specifically greater than or equal to 8% by weight. Said amount is generally less than or equal to 50% by weight, often less than or equal to 45% by weight and more specifically less than or equal to 40% by weight.

The amount of esters of the chlorohydrin in the mixture containing the chlorohydrin and esters of the chlorohydrin, expressed in % by weight of the chlorohydrin, is generally greater than or equal to 1% by weight, often greater than or equal to 2% by weight and more specifically greater than or equal to 3% by weight. Said amount is generally less than or equal to 30% by weight, often less than or equal to 25% by weight and more specifically less than or equal to 20% by weight.

The mixture containing the chlorohydrin and esters of the chlorohydrin may also contain compounds other than the chlorohydrin and the esters of the chlorohydrin, as defined above, and, among others, the polyhydroxylated aliphatic hydrocarbon, by-products, the chlorinating agent, the organic acid used in step (a) of the process according to the invention, and the solvent optionally used.

The amount of these other compounds in the mixture containing the chlorohydrin and the esters of the chlorohydrin is generally less than or equal to 95% by weight, often less than or equal to 90% by weight and more specifically less than or equal to 80% by weight. Said amount is generally greater than or equal to 20% by weight, often greater than or equal to 30% by weight and more specifically greater than or equal to 40% by weight.

Step (c) of the process according to the invention is preferably carried out without supplying chlorinating agent other than residues of chlorinating agent which have possibly not reacted in step (a).

Step (c) of the process according to the invention is carried out at a temperature greater than or equal to 20° C., preferably greater than or equal to 40° C., more preferably greater than or equal to 60° C. and with very particular preference greater than or equal to 100° C. This temperature is generally less or equal to 180° C., preferably less than or equal to 175° C. and with particular preference less than or equal to 160° C.

Step (c) of the process according to the invention is generally carried out at an absolute pressure greater than or equal to 0.01 bar, preferably greater than or equal to 0.05 bar and with particular preference greater than or equal to 0.1 bar. This pressure is generally less than or equal to 50 bar, preferably less than or equal to 10 bar and with particular preference less than or equal to 5 bar.

The duration of step (c) of the process according to the invention is generally greater than or equal to 2 min, preferably greater than or equal to 5 min and with very particular preference greater than or equal to 10 min. This duration is generally less than or equal to 20 h, preferably less than or equal to 5 h and with very particular preference less than or equal to 2 h.

The molar ratio between the polyhydroxylated aliphatic hydrocarbon and the esters of the chlorohydrin in step (c) of the process according to the invention is generally greater than or equal to 0.01 mol/mol, preferably greater than or equal to 0.02 mol/mol and with very particular preference greater than or equal to 0.05 mol/mol. Said molar ratio is generally less than or equal to 20 mol/mol, preferably less than or equal to 10 mol/mol and with very particular preference less than or equal to 5 mol/mol.

Without wishing to be tied by any theoretical explanation, it is thought that the polyhydroxylated aliphatic hydrocarbon reacts at least partly with the esters of chlorohydrin present in the mixture obtained in step (a), so as to form the chlorohydrin and esters of the polyhydroxylated aliphatic hydrocarbon. By "partly" is meant that the part of esters of the chlorohydrin which reacts with the polyhydroxylated aliphatic hydrocarbon during step (c) is at least 1 mol % of the esters of the chlorohydrin present prior to the addition of the polyhydroxylated aliphatic hydrocarbon, preferably at least 2 mol % and with very particular preference at least 5 mol %.

Without wishing to be tied by any theoretical explanation, it is thought that, when the organic acid used in step (a) is a catalyst for the reaction between the polyhydroxylated aliphatic hydrocarbon and the chlorinating agent, said acid is located initially at least partly in the esters of the chlorohydrin that are formed in step (a) and finally at least partly in the esters of the polyhydroxylated aliphatic hydrocarbon that are formed in the course of step (c). It is also thought that said acid is more readily separable from the chlorohydrin when the acid is in the form of esters of the polyhydroxylated aliphatic hydrocarbon than when it is in the form of esters of the chlorohydrin. Its recycling to step (a) of the process according to the invention is facilitated as a result.

The esters of the polyhydroxylated aliphatic hydrocarbon may be present in step (a) of the process according to the invention.

Without wishing to be tied by any theoretical explanation, it is thought that the solubility of the chlorinating agent in the fraction of the mixture withdrawn in step (a) is higher after the addition of the polyhydroxylated aliphatic hydrocarbon, and that the separation of the chlorinating agent and of the chlorohydrin is facilitated as a result.

The treatments in the steps subsequent to step (a) may be intended to separate the chlorohydrin from the other compounds of the reaction mixture, and the addition of the polyhydroxylated aliphatic hydrocarbon may be made before or during these treatments. These treatments may be, for example, evaporation, stripping or distillation operations.

In a first embodiment of the process for preparing a chlorohydrin according to the invention, a fraction of the mixture obtained in step (a) is withdrawn and, during its withdrawal, the polyhydroxylated aliphatic hydrocarbon is added thereto, so as to give a treated fraction.

In a first variant of this first embodiment, the fraction thus treated may be subjected to at least one subsequent separating operation, such as an evaporation, stripping or distillation operation.

In a second variant of this first embodiment, the fraction thus treated may be subjected to an evaporation treatment in an evaporator, optionally in the presence of a gaseous stream, so as to remove the compounds which are more volatile than the chlorohydrin and than the esters of the chlorohydrin, and to obtain a part concentrated with chlorohydrin and with esters of the chlorohydrin, and polyhydroxylated aliphatic hydrocarbon is added to the evaporator.

In a third variant of this first embodiment, the fraction thus treated may be subjected to a stripping and/or distillation treatment in a stripping and/or distillation column, so as to give a part concentrated with chlorohydrin, and polyhydroxylated aliphatic hydrocarbon is added to the stripping and/or distillation column.

In a fourth variant, the fraction thus treated may be subjected to an evaporation treatment in an evaporator, optionally in the presence of a gaseous stream, so as to remove the compounds which are more volatile than the chlorohydrin and than the esters of the chlorohydrin and to obtain a part concentrated with chlorohydrin and with esters of the chlorohydrin, and polyhydroxylated aliphatic hydrocarbon is added to the evaporator, and the part concentrated with chlorohydrin and with esters of the chlorohydrin may be subsequently subjected to a stripping and/or distillation treatment in a stripping and/or distillation column so as to give a part concentrated with chlorohydrin, and polyhydroxylated aliphatic hydrocarbon is added to the stripping and/or distillation column.

In a second embodiment of the process for preparing the chlorohydrin, a fraction of the mixture obtained in step (a) is withdrawn, this fraction is subjected to an evaporation treatment in an evaporator, optionally in the presence of a gaseous stream, so as to remove the compounds which are more volatile than the chlorohydrin and than the esters of the chlorohydrin, and to give a part concentrated with chlorohydrin and with esters of the chlorohydrin, and polyhydroxylated aliphatic hydrocarbon is added to the evaporator.

In a first variant of this second embodiment, the part concentrated with chlorohydrin and with esters of the chlorohydrin may be subjected to at least one subsequent separating operation, such as a stripping and/or distillation operation.

In a second variant of this second embodiment, the part concentrated with chlorohydrin and with esters of the chlorohydrin may be subjected to a stripping and/or distillation treatment in a stripping and/or distillation column so as to give a part concentrated with chlorohydrin, and polyhydroxylated aliphatic hydrocarbon is added to the stripping and/or distillation column.

In a third embodiment of the process for preparing the chlorohydrin, a fraction of the mixture obtained in step (a) is withdrawn, this fraction is subjected to a stripping and/or distillation treatment in a stripping and/or distillation column so as to give a portion concentrated with chlorohydrin, and the polyhydroxylated aliphatic hydrocarbon is added to the distillation column.

By evaporation is meant the separation of a substance by heating, optionally under reduced pressure.

By stripping is meant the separation of a substance by entrainment by means of the vapour of a body which does not dissolve said substance. In the process according to the invention, said body may be any compound which is inert to the chlorohydrin, such as, for example, water vapour, air, nitrogen and carbon dioxide. These same compounds may constitute the gaseous stream which is optionally present in the evaporation treatment.

By distillation is meant the direct passage from the liquid state to the gaseous state, followed by condensation of the vapours obtained. By fractional distillation is meant a series of distillations carried out on the vapours successively condensed. Fractional distillation treatment is preferred.

The stripping and distillation treatments may be combined, for example in a stripping column surmounted by a distilling section.

The addition of the polyhydroxylated aliphatic hydrocarbon may be made at any location on the stripping and/or distillation column. Preference is given to adding the polyhydroxylated aliphatic hydrocarbon at a level higher than the level at which the fraction of mixture withdrawn in step (a) is supplied. Without wishing to be tied by a theoretical explanation, it is thought that this procedure allows the contact time between the polyhydroxylated aliphatic hydrocarbon and the esters of the chlorohydrin to be prolonged and hence allows the formation of the chlorohydrin and of esters of the polyhydroxylated aliphatic hydrocarbon.

These treatments may be conducted in batch mode or in continuous mode. Continuous mode is preferred.

At the outcome of the treatments, at least one first part enriched with chlorohydrin and at least one second part depleted in chlorohydrin and in esters of the chlorohydrin and enriched with esters of the polyhydroxylated aliphatic hydrocarbon is recovered.

The amount of chlorohydrin in the first part is generally greater than or equal to 10% by weight, often greater than or equal to 15% by weight and more specifically greater than or equal to 20%. This amount is generally less than or equal to 99.9% by weight, often less than or equal to 99.5% by weight and more specifically less than or equal to 99% by weight.

The amount of esters of the chlorohydrin in the second part, expressed in percent by weight of the chlorohydrin, is generally less than or equal to 25% by weight, often less than or equal to 20% by weight. This amount is generally greater than or equal to 0.5% by weight, often greater than or equal to 1% by weight and more specifically greater than or equal to 2% by weight.

The amount of esters of the polyhydroxylated aliphatic hydrocarbon in the second part, expressed in percent by weight of the polyhydroxylated aliphatic hydrocarbon, is generally greater than or equal to 0.2% by weight, often greater than or equal to 0.5% by weight and more specifically greater than or equal to 1% by weight. This amount is generally less than or equal to 15% by weight, often less than or equal to 10% by weight and more specifically less than or equal to 5% by weight.

The second part may optionally be recycled to step (a) of the process according to the invention.

The chlorohydrin obtained in the process according to the invention may include a heightened amount of halogenated ketones, in particular of chloroacetone, as described in the patent application FR 05.05120 of 20/05/2005, filed in the name of the applicant, and the content of which is incorporated here by reference. The halogenated ketone content may be reduced by subjecting the chlorohydrin obtained in the process according to the invention to an azeotropic distillation in the presence of water or by subjecting the chlorohydrin to a dehydrochlorination treatment as described in this application from page 4 line 1 to page 6 line 35.

Particular mention is made of a process for preparing an epoxide wherein halogenated ketones are formed as by-products and which comprises at least one treatment of removal of at least a portion of the halogenated ketones formed. Mention is made more particularly of a process for preparing an epoxide by dehydrochlorinating a chlorohydrin of which at least one fraction is prepared by chlorinating a polyhydroxylated aliphatic hydrocarbon, an ester of a polyhydroxylated aliphatic hydrocarbon or a mixture thereof, a treatment of dehydrochlorination and a treatment by azeotropic distillation of a water/halogenated ketone mixture, which are intended to remove at least a portion of the halogenated ketones formed, and a process for preparing epichlorohydrin wherein the halogenated ketone formed is chloroacetone.

The chlorohydrin obtained in the process according to the invention may be subjected to a dehydrochlorination reaction in order to produce an epoxide, as described in the patent applications WO 2005/054167 and FR 05.05120, both filed in the name of SOLVAY SA.

The term "epoxide" is used herein to describe a compound containing at least one oxygen bridged on a carbon-carbon bond. Generally speaking, the carbon atoms of the carbon-carbon bond are adjacent and the compound may contain atoms other than carbon atoms and oxygen atoms, such as hydrogen atoms and halogens. The preferred epoxides are ethylene oxide, propylene oxide and epichlorohydrin.

The dehydrochlorination of the chlorohydrin may be carried out as described in the application entitled "Process for preparing an epoxide starting from a polyhydroxylated aliphatic hydrocarbon and a chlorinating agent", filed in the name of SOLVAY SA on the same day as the present application, and the content of which is incorporated here by reference.

Particular mention is made of a process for preparing an epoxide wherein a reaction mixture resulting from the reaction between a polyhydroxylated aliphatic hydrocarbon, an ester of a polyhydroxylated aliphatic hydrocarbon or a mixture thereof with a chlorinating agent, the reaction mixture containing at least 10 g of chlorohydrin per kg of reaction mixture, is subjected to a subsequent chemical reaction without intermediate treatment.

Mention is also made of the preparation of an epoxide that comprises the following steps: (a) a polyhydroxylated aliphatic hydrocarbon, an ester of a polyhydroxylated aliphatic hydrocarbon or a mixture thereof is reacted with a chlorinating agent and an organic acid so as to form the chlorohydrin and chlorohydrin esters in a reaction mixture containing the polyhydroxylated aliphatic hydrocarbon, the ester of polyhydroxylated aliphatic hydrocarbon, water, the chlorinating agent and the organic acid, the reaction mixture containing at least 10 g of chlorohydrin per kg of reaction mixture, (b) at least a fraction of the reaction mixture obtained in step (a), this fraction having the same composition as the reaction mixture obtained in step (a), is subjected to one or more treatments in steps subsequent to step (a), and (c) a basic compound is added to at least one of the steps subsequent to step (a) in order to react at least partly with the chlorohydrin, the chlorohydrin esters, the chlorinating agent and the organic acid so as to form the epoxide and salts.

The process for preparing the chlorohydrin according to the invention may be integrated within an overall plan for preparation of an epoxide, as described in the application entitled "Process for preparing an epoxide starting from a chlorohydrin", filed in the name of SOLVAY SA on the same day as the present application, and the content of which is incorporated here by reference.

Particular mention is made of a process for preparing an epoxide that comprises at least one step of purification of the epoxide formed, the epoxide being at least partly prepared by a process of dehydrochlorinating a chlorohydrin, the latter being at least partly prepared by a process of chlorinating a polyhydroxylated aliphatic hydrocarbon, an ester of a polyhydroxylated aliphatic hydrocarbon or a mixture thereof.

When the chlorohydrin is dichloropropanol, the process according to the invention may be followed by preparation of epichlorohydrin by dehydrochlorination of dichloropropanol, and the epichlorohydrin may be used in the production of epoxy resins.

In the process according to the invention, when the polyhydroxylated aliphatic hydrocarbon is glycerol, it may contain glycerol esters as defined earlier on above. The invention likewise provides a process for preparing dichloropropanol, comprising the following steps:

(a) glycerol and/or glycerol esters are/is reacted with hydrogen chloride or hydrochloric acid and an organic acid so as to give a mixture containing dichloropropanol and dichloropropanol esters (b) glycerol is added to the fraction obtained in step (a), so as to react at least partly with the dichloropropanol esters so as to form, at least partly, glycerol esters.

FIG. 1 shows a particular scheme of plant which can be used for implementing the separation process according to the invention.

A reactor (4) is supplied in continuous mode or in batch mode with the polyhydroxylated aliphatic hydrocarbon, an ester of a polyhydroxylated aliphatic hydrocarbon or a mixture thereof via line (1), and with catalyst via line (2); the chlorinating agent is supplied in continuous mode or in batch mode via line (3); a distillation column (6) is supplied via line (5) with vapours produced in reactor (4); a stream is taken off from column (6) via line (7) and is introduced into a condenser (8); and the stream obtained from the condenser is introduced via line (9) into a phase separator (10), in which the aqueous and organic phases are separated. A fraction of the separated aqueous phase is optionally recycled via line (11) to the top of the column in order to maintain the reflux. Fresh water may be added via line (12) to the top of the column in order to maintain the reflux. The production of the chlorohydrin is distributed between the organic phase taken off via line (14) and the aqueous phase taken off via line (13). The residue from column (6) may be recycled to reactor (4) via line (15). A fraction of the heavy products is taken off from reactor (4) via the purge (16) and is introduced via line (17) into an evaporator (18), in which a partial evaporation operation is carried out, for example, by heating or by gas scavenging with nitrogen or with water vapour; the gaseous phase containing the majority of the chlorinating agent from stream (17) is recycled via line (19) to column (6) or via line (20) to reactor (4); a distillation or stripping column (22) is supplied with the liquid phase coming from evaporator (18) via line (21); line (21) and/or distillation column (22) and/or evaporator (18) and/or line (17) are supplied with polyhydroxylated aliphatic hydrocarbon via, respectively, line (32) and/or line (31) and/or line (33) and/or line (34); the majority of the chlorohydrin is collected at the top of column (22) via line (23), and the residue, which contains the esters of the polyhydroxylated aliphatic hydrocarbon, is introduced via line (24) into the filtering unit (25), in which the liquid and solid phases are separated; and the liquid phase is recycled via line (26) to reactor (4). The solid may be taken off from filtering unit (25) via line (27) in the form of a solid or a solution. Solvents may be added to filtering unit (25) via lines (28) and (29) for the washing and/or dissolving of the solid, and may be taken off via line (27). Optionally a stream is taken off from purge (16) and introduced via line (30) into the filtering column (25). Evaporator (18) and distillation column (22) are in that case short-circuited. In another option, where is it not necessary to remove a solid compound from the process, the liquid taken off at the bottom of column (22) is directly returned via line (33) to reactor (4). Filtering unit (25) and the lines connected to it are in that case no longer indispensable.

In the process according to the invention, the polyhydroxylated aliphatic hydrocarbon is preferably glycerol and the chlorohydrin is preferably dichloropropanol.

The examples below are intended to illustrate the invention without, however, imposing any limitation thereon.

EXAMPLE 1

Not in Accordance with the Invention

A reaction mixture containing 61 g of dichloropropanol, 20.5 g of monochlorohydrin of glycerol (MCG), 0.7 g of glycerol (GLC), 6.3 g of adipic acid, 0.4 g of chlorinated diglycerol, 23.3 g of dichloropropanol adipate, 42 g of MCG adipate, 1.6 g of GLC adipate, 4.9 g of water and 0.3 g of HCl was subjected to evaporation on a rotary evaporator at 165° C. under 0.04 bar. After 45 minutes, 61 g of the dichloropropanol were recovered in the evaporated liquid, and 6 g of dichloropropanol and 12 g of dichloropropanol adipate in the residue. 2 g of glycerol adipate were recovered in the residue.

EXAMPLE 2

In Accordance with the Invention

A reaction mixture containing 61 g of dichloropropanol, 20.5 g of MCG, 0.7 g of GLC, 6.3 g of adipic acid, 0.4 g of chlorinated diglycerol, 23.3 g of dichloropropanol adipate, 42 g of MCG adipate, 1.6 g of GLC adipate, 4.9 g of water and 0.3 g of HCl is admixed with 19 g of glycerol before being subjected to evaporation on a rotary evaporator at 165° C. under 0.04 bar. After 45 minutes, 69 g of the dichloropropanol are recovered in the evaporated liquid, and there remain 4 g of dichloropropanol and also a trace of dichloropropanol adipate in the residue. 22 g of glycerol adipate are found in the residue.

The invention claimed is:

1. A process for preparing a chlorohydrin, comprising:
(a) a polyhydroxylated aliphatic hydrocarbon, an ester of a polyhydroxylated aliphatic hydrocarbon or a mixture thereof is reacted with a chlorinating agent and an organic acid so as to give a mixture comprising the chlorohydrin and esters of the chlorohydrin
(b) at least part of the mixture obtained in (a) is subjected to one or more treatments subsequent to (a)
(c) polyhydroxylated aliphatic hydrocarbon is added to a mixture comprising one or more esters of the chlorohydrin subsequent to (a), so as to react, at a temperature greater than or equal to 20° C., with the one or more esters of the chlorohydrin, so as to form, at least partly, esters of the polyhydroxylated aliphatic hydrocarbon,
wherein the reaction of the polyhydroxylated aliphatic hydrocarbon with the one or more esters of the chlorohydrin is carried out at a molar ratio between the polyhydroxylated aliphatic hydrocarbon and the one or more esters of the chlorohydrin that is greater than or equal to 0.01 and less than or equal to 20 mol/mol, and
wherein either
during (b), a fraction of the mixture obtained in (a) is withdrawn, this fraction is subjected to an evaporation treatment (I) in an evaporator, optionally in the presence of a gaseous stream, so as to remove the compounds more volatile than the chlorohydrin and than the one or more esters of the chlorohydrin and to obtain a part concentrated with chlorohydrin and with one or more esters of the chlorohydrin, and the polyhydroxylated aliphatic hydrocarbon is added to the withdrawn fraction of the mixture, prior to the evaporation treatment, and/or to the evaporator at a level higher than the level at which said evaporator is supplied with the fraction withdrawn in (a),
or
during (b), a fraction of the mixture obtained in (a) is withdrawn, this fraction is subjected to a stripping and/or distillation treatment (II) in a stripping and/or distillation column, so as to give a portion concentrated with chlorohydrin, and the polyhydroxylated aliphatic hydrocarbon is added to the withdrawn fraction of the mixture, prior to the stripping and/or distillation treatment, and/or to the stripping and/or distillation column at a level higher than the level at which said column is supplied with the fraction withdrawn in (a).

2. The process according to claim 1, according to which, during (b), a fraction of the mixture obtained in (a) is withdrawn, this fraction is subjected to an evaporation treatment (I) in an evaporator, optionally in the presence of a gaseous stream, so as to remove the compounds more volatile than the chlorohydrin and than the esters of the chlorohydrin and to obtain a part concentrated with chlorohydrin and with esters of the chlorohydrin, and the polyhydroxylated aliphatic hydrocarbon is added to the withdrawn fraction of the mixture, prior to the evaporation treatment, and/or to the evaporator at a level higher than the level at which said evaporator is supplied with the fraction withdrawn in (a).

3. The process according to claim 1, according to which, during (b), a fraction of the mixture obtained in (a) is withdrawn, this fraction is subjected to a stripping and/or distillation treatment (II) in a stripping and/or distillation column, so as to give a portion concentrated with chlorohydrin, and the polyhydroxylated aliphatic hydrocarbon is added to the withdrawn fraction of the mixture, prior to the stripping and/or distillation treatment, and/or to the stripping and/or distillation column at a level higher than the level at which said column is supplied with the fraction withdrawn in (a).

4. The process according to claim 2, according to which, during (b), a section of the part concentrated with chlorohydrin and with one or more esters of the chlorohydrin, obtained in the treatment (I), is withdrawn, this section is subjected to a stripping and/or distillation treatment in a stripping and/or distillation column (III), and the polyhydroxylated aliphatic hydrocarbon is added to the withdrawn section, prior to the stripping and/or distillation treatment, and/or to the stripping and/or distillation column at a level higher than the level at which said column is supplied with the part withdrawn in the treatment (I).

5. The process according to claim 1, wherein the reaction of the polyhydroxylated aliphatic hydrocarbon with the one or more esters of the chlorohydrin is carried out at a temperature greater than or equal to 40° C. and less than or equal to 180° C., at an absolute pressure greater than or equal to 0.01 bar and less than or equal to 50 bar, for a time greater than or equal to 2 min and less than or equal to 20 h and at a molar ratio between the polyhydroxylated aliphatic hydrocarbon and the esters of the chlorohydrin which is greater than or equal to 0.05 and less than or equal to 5 mol/mol.

6. The process according to claim 1, wherein the polyhydroxylated aliphatic hydrocarbon, the ester of polyhydroxylated aliphatic hydrocarbon or the mixture thereof is obtained starting from renewable raw materials.

7. The process according to claim 1, wherein the chlorinating agent is a combination of gaseous hydrogen chloride with an aqueous solution of hydrogen chloride, or is an aqueous solution of hydrogen chloride.

8. The process according to claim 1 according to which, at the outcome of the subsequent treatments, at least a first part enriched with chlorohydrin and at least a second part depleted in chlorohydrin and in chlorohydrin esters and enriched with esters of the polyhydroxylated aliphatic hydrocarbon are recovered, and wherein the second part is recycled to (a).

9. The process according to claim 1, according to which the polyhydroxylated aliphatic hydrocarbon is at least one selected from the group consisting of ethylene glycol, propylene glycol, chloropropanediol, glycerol and mixtures of at least two thereof.

10. The process according to claim 1, according to which the chlorohydrin is selected from the group consisting of chloroethanol, chloropropanol, chloropropanediol, dichloropropanol and mixtures of at least two thereof.

11. The process according to claim 9, according to which the polyhydroxylated aliphatic hydrocarbon is glycerol and the chlorohydrin is dichloropropanol.

12. The process according to claim 11, followed by preparation of epichlorohydrin by dehydrochlorination of dichloropropanol.

13. The process according to claim 12, further comprising the preparation of an epoxy resin by reacting the epichlorohydrin.

14. The process according to claim 1, wherein the reaction of the polyhydroxylated aliphatic hydrocarbon with the one or more esters of the chlorohydrin is carried out at a temperature greater than or equal to 40° C. and less than or equal to 180° C., at an absolute pressure greater than or equal to 0.01 bar and less than or equal to 50 bar, for a time greater than or equal to 2 min and less than or equal to 20 h.

\* \* \* \* \*